United States Patent
Vembar et al.

(10) Patent No.: US 9,955,934 B2
(45) Date of Patent: May 1, 2018

(54) DYNAMIC ACQUISITION SAMPLING RATE FOR COMPUTED TOMOGRAPHY PERFUSION (CTP) IMAGING

(75) Inventors: Mani Vembar, Twinsburg, OH (US); Thomas Bernard Ivanc, Willoughby, OH (US); Sunny Virmani, Willoughby Hills, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 501 days.

(21) Appl. No.: 13/879,647

(22) PCT Filed: Oct. 17, 2011

(86) PCT No.: PCT/IB2011/054582
§ 371 (c)(1),
(2), (4) Date: Apr. 16, 2013

(87) PCT Pub. No.: WO2012/052901
PCT Pub. Date: Apr. 26, 2012

(65) Prior Publication Data
US 2013/0211245 A1     Aug. 15, 2013

Related U.S. Application Data

(60) Provisional application No. 61/394,508, filed on Oct. 19, 2010.

(51) Int. Cl.
*A61B 6/00* (2006.01)
*A61B 6/03* (2006.01)

(52) U.S. Cl.
CPC ............ *A61B 6/481* (2013.01); *A61B 6/03* (2013.01); *A61B 6/032* (2013.01); *A61B 6/467* (2013.01);
(Continued)

(58) Field of Classification Search
USPC ................................. 250/370.09
See application file for complete search history.

(56) References Cited

U.S. PATENT DOCUMENTS

| 5,917,883 A | 6/1999 | Khutoryansky et al. |
| 8,184,768 B2 * | 5/2012 | Honda et al. ........ 378/16 |

(Continued)

FOREIGN PATENT DOCUMENTS

| EP | 2087843 A1 | 8/2009 |
| WO | 2005073915 A2 | 8/2005 |

(Continued)

OTHER PUBLICATIONS

Cademartiri, Filippo, et al. "Intravenous Contrast Material Administration at 16—Detector Row Helical CT Coronary Angiography: Test Bolus versus Bolus-tracking Technique 1." Radiology 233.3 (2004): 817-823.*

(Continued)

*Primary Examiner* — Amelie R Gillman
*Assistant Examiner* — Carolyn Pehlke

(57) ABSTRACT

A method includes dynamically varying a data acquisition sample rate between at least two data acquisition sample rates during a contrast enhanced perfusion scan based on a level of contrast in image data generated during the scan. A system includes a computed tomography scanner and a console that controls the scanner based on a scan protocol, wherein the console dynamically varies a data acquisition sample rate of scanner during a contrast enhanced perfusion scan based on a level of contrast in the image data generated during the scan. A method for optimizing dose of a scan includes reducing a data acquisition sampling rate during at least a sub-portion of the scan in which a state of interest is not being scanned.

19 Claims, 2 Drawing Sheets

(52) U.S. Cl.
CPC .............. *A61B 6/486* (2013.01); *A61B 6/507* (2013.01); *A61B 6/541* (2013.01); *A61B 6/542* (2013.01)

(56) References Cited

U.S. PATENT DOCUMENTS

| | | | |
|---|---|---|---|
| 2004/0101085 A1 | 5/2004 | Edic | |
| 2006/0233296 A1* | 10/2006 | Wakai et al. | 378/8 |
| 2007/0092055 A1 | 4/2007 | Vires et al. | |
| 2008/0123812 A1* | 5/2008 | Sabol et al. | 378/95 |
| 2009/0022265 A1* | 1/2009 | Takase et al. | 378/8 |
| 2009/0297008 A1 | 12/2009 | Taxt et al. | |
| 2010/0292570 A1* | 11/2010 | Tsukagoshi | 600/431 |

FOREIGN PATENT DOCUMENTS

| | | | | |
|---|---|---|---|---|
| WO | | 2008120119 A1 | 10/2008 | |
| WO | WO 2009045368 A1 * | | 4/2009 | A61B 6/00 |

OTHER PUBLICATIONS

McCollough, Cynthia H., et al. "Strategies for reducing radiation dose in CT." Radiologic Clinics of North America 47.1 (2009): 27-40.*

Rudin, et al., Nonlinear total variation based noise removal algorithms, Physica D, 1992, pp. 259-268, vol. 60, Elsevier Science Publishers B.V.

Di Bella, et al., Temporal Sampling of MRI Myocardial Perfusion Studies: Effects on Three Analysis Methods, Proc. Intl., Soc., Mag. Reson. Med., 2003, p. 703, vol. 11.

Wintermark, et al., Dynamic Perfusion CT: Optimizing the Temporal Resolution and Contrast Volume for Calculation of Perfusion CT Parameters in Stroke Patients, AJNR Am J Neuroradiol, May 2004, pp. 720-729, vol. 25, American Society of Neuroradiology.

Wintermark, et al., Comparative Overview of Brain Perfusion Imaging Techniques, Stroke Journal of the American Heart Association, originally published Aug. 11, 2005, pp. Cover + e83-e99, vol. 36.

Le, et al., A variational approach to reconstructing images corrupted by Poisson noise, UCLA CAM Report 05-49, Sep. 21, 2005, 10 sheets.

Cohnen, et al., Radiation Exposure of Patients in Comprehensive Computed Tomography of the Head in Acute Stroke, AJNR AM J Neuroradiol, Sep. 2006, pp. 1741-1745, col. 27, www.ajnr.org.

Yang, et al., Multiphase CT Angiography versus Single-Phase CT Angiograpy: Comparison of Image Quality and Radiation Dose, AJNR, Aug. 2008, pp. 1288-1295, vol. 29, www.ajnr.org.

Hsu, et al., 2026 Tradeoffs between spatial coverage and dynamic temperal resolution in quantitative first-pass perfusion imaging meeting abstract, Journal of Cardiovascular Magnetic Resonance, , Oct. 22, 2008, 4 sheets, vol. 10, suppl 1, http://jcmr-online.com/content/10/S1/A295.

Goh, et al., Effect of Temporal Interval Between Scan Acquisitions on Quantitative Vascular Parameters in Colorectal Cancer:Implications for Helical Volumetric Perfusion CT Techniques, CT Imaging Original Research, AJR, Dec. 2008, pp. W288-W292, vol. 191, American Roentgen Ray Society.

Konstas, et al., Theoretic Basis and Technical Implementations of CT Perfusion in Acute Ischemic Stroke, Part 2: Technical Implications, Physics Review AJNR Am J Neuroradiol, May 2008, pp. 885-892, vol. 30, www.ajnr.org.

Tognolini, et al., Body Tumor CT Perfusion Protocols: Optimization of Acquisition Scan Parameters in a Rat Tumor Model, Original Research, Radiology, Jun. 2009, pp. 712-720 (11 sheets attached), vol. 251, No. 3, radiology.rsnajnls.org.

* cited by examiner

DYNAMIC ACQUISITION SAMPLING RATE FOR COMPUTED TOMOGRAPHY PERFUSION (CTP) IMAGING

CROSS REFERENCE TO RELATED APPLICATIONS

This application is a national filing of PCT application Serial No. PCT/IB2011/054582, filed Oct. 17, 2011, published as WO 2012/052901 A1 on Apr. 26, 2012, which claims the benefit of U.S. provisional application Ser. No. 61/394,508 filed Oct. 19, 2010, which is incorporated herein by reference.

The following generally relates to perfusion imaging and is described with application to computed tomography perfusion (CTP) and in particular to employing a dynamic acquisition sampling rate in connection with CTP scanning.

Computed tomography perfusion (CTP) is a medical imaging technique that is used to diagnose, characterize lesions and potentially influence patient care as well as in determining the outcome of therapy. Generally, a CTP scan shows the transit of an administered contrast agent through vascular tissue such as vessels and organs. An intravenous contrast agent bolus is administered to the patient and the patient is scanned. The contrast agent causes the x-ray density to temporarily increase as the contrast agent flows through the vascular tissue. The scan includes acquiring data over multiple intervals covering contrast agent arrival, uptake and wash out through vascular structure of interest.

Analysis of the acquired data can be used to determine perfusion status of vascular tissue of interest based on the observations of contrast agent dynamics in the scan field of view. Such analysis may include determining various perfusion related information such as a time-attenuation curve, blood flow, blood volume, mean transit time, and time to peak. This information can be used to identify ischemic tissue and/or differentiate between irreversibly damaged tissue (necrotic tissue, or the ischemic core) and potentially reversibly damaged tissue (at-risk tissue, or the ischemic penumbra).

Unfortunately, the patient is exposed to radiation not only during the period of contrast agent uptake and wash out, but also before uptake in order to establish a baseline value and detect arrival and wash out relative to the baseline value. Furthermore, a typical exam involves repeated scans of the same location at pre-defined intervals over a period of time to observe contrast uptake and wash-out and thus such scans have been considered high dose and not well-suited for screening and/or routine clinical practice. In addition, patients who typically need such exams also need several follow-up CT exams, which increases the cumulative radiation dose. Moreover, simply reducing the overall sampling rate may potentially negatively impact the aforementioned quantitative perfusion measurements.

Aspects of the present application address the above-referenced matters and others.

According to one aspect, a method includes dynamically varying a data acquisition sample rate between at least two different data acquisition sample rates during a contrast enhanced perfusion scan based on a level of contrast in image data generated during the scan.

According to another aspect, a system includes a computed tomography scanner and a console that controls the scanner based on a scan protocol, wherein the console dynamically varies a data acquisition sample rate of a scans during a contrast enhanced perfusion scan based on a level of contrast in the image data generated during the scanner.

According to another aspect, a method for optimizing dose of a scan includes reducing a data acquisition sampling rate during at least a sub-portion of the scan in which a state of interest is not being scanned.

According to another aspect, a perfusion imaging method includes acquiring data at a first sampling rate until contrast uptake has been determined and acquiring data at a second sampling rate, which is greater than the first sampling rate, during contrast uptake.

The invention may take form in various components and arrangements of components, and in various steps and arrangements of steps. The drawings are only for purposes of illustrating the preferred embodiments and are not to be construed as limiting the invention.

Figure 1:
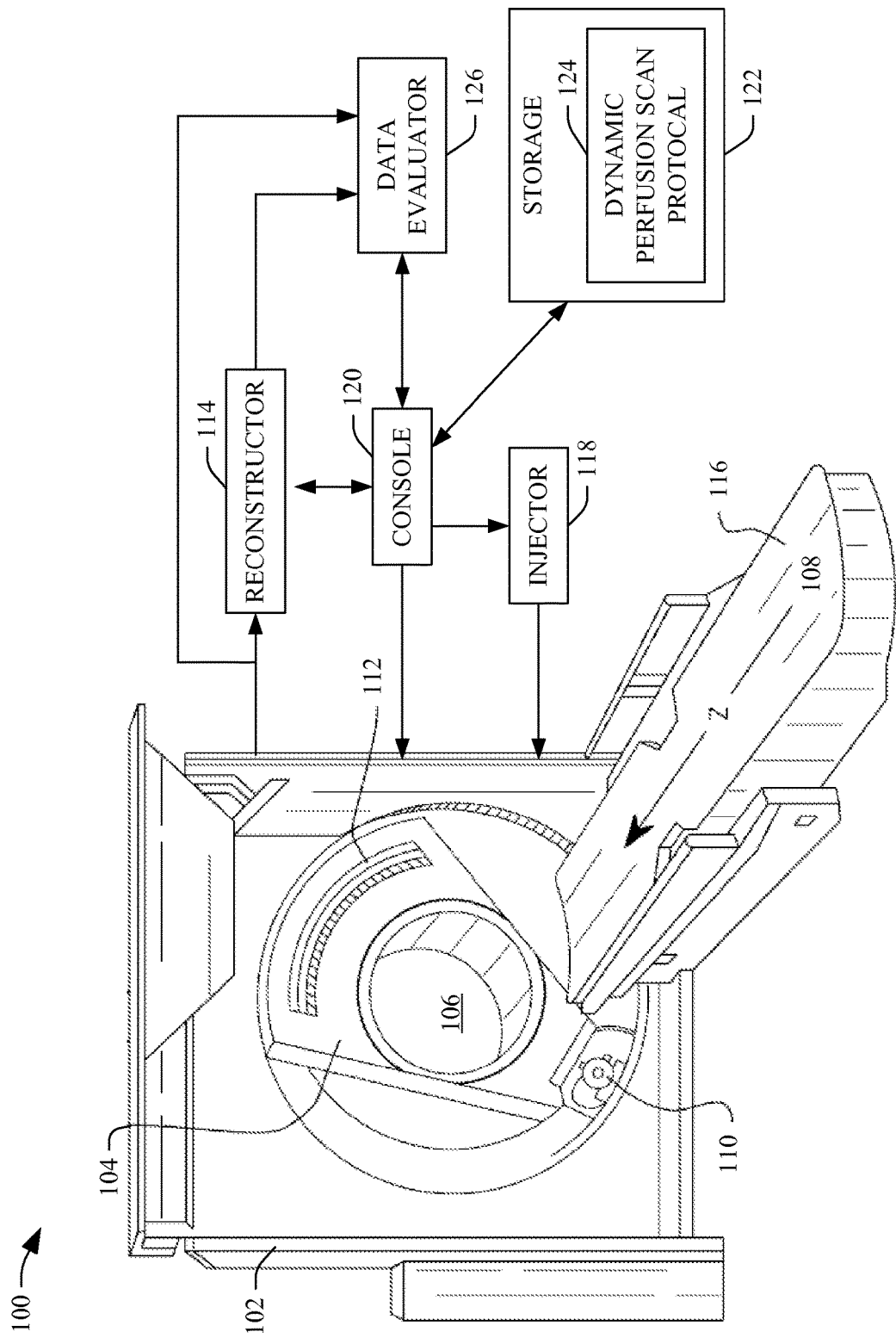
FIG. 1 illustrates an imaging system.

FIG. 1 illustrates an imaging system such as a computed tomography (CT) scanner 100. The scanner 100 includes a stationary gantry 102 and a rotating gantry 104, which is rotatably supported by the stationary gantry 102. The rotating gantry 104 rotates around an examination region 106 about a longitudinal or z-axis 108. A patient support 116, such as a couch, supports a patient in the examination region 106 and is movable along the z-axis 108 in coordination with the rotation of the rotating gantry 104 to facilitate helical, axial, or other desired scanning trajectories.

A radiation source 110, such as an x-ray tube, is supported by and rotates with the rotating gantry 104 around the examination region 106. The radiation source 110 emits generally fan, wedge, or cone shaped radiation that traverses the examination region 106. A radiation sensitive detector array 112 detects photons emitted by the radiation source 110 that traverse the examination region 106 and generates projection data indicative of the detected radiation.

An injector 118 is configured to inject or administer a material such as one or more contrast agents to an object (e.g., a phantom) or subject, such as a human or animal patient, to be scanned. A contrast agent can additionally or alternatively be manually administered by a clinician or the like. Where the contrast agent is manually administered, the injector 118 can be omitted. A reconstructor 114 reconstructs the projection data and generates volumetric image data indicative of the examination region 106.

A data evaluator 126 evaluates the projection data and/or the reconstructed image data. In the illustrated embodiment, and as described in greater detail below, the data evaluator 126 evaluates the projection and/or image data and determines a presence of and/or degree of contrast agent in tissue of interest represented in the projection and/or image data, and generates a signal indicative thereof.

A general purpose computing system serves as an operator console 120. Software resident on the console 120 allows the operator to control the operation of the system 100, for example, by allowing the operator to select a scan protocol such as a dynamic perfusion scan protocol 124 from storage 122, etc. The data evaluator 126 can be part of the console 120 and/or other computing system including a computer.

In one instance, the console 120, when executing the dynamic perfusion scan protocol 124, dynamically adjusts the data acquisition sampling rate of a scan based on the signal from the data evaluator 126. For example, in the context of a contrast enhanced scan, the console 120 may decrease the data acquisition sampling rate when scanning until the contrast reaches tissue of interest, and then increase the data acquisition sampling rate when scanning the tissue of interest as the contrast is traversing the tissue of interest.

Such control allows for reducing overall dose while maintaining a given data acquisition sample rate during uptake and/or wash out. Furthermore, such control allows for maintaining a given dose while increasing the data acquisition sample rate during uptake and/or wash out. Furthermore, such control allows for optimizing a scan length for a given dose.

Figure 2:
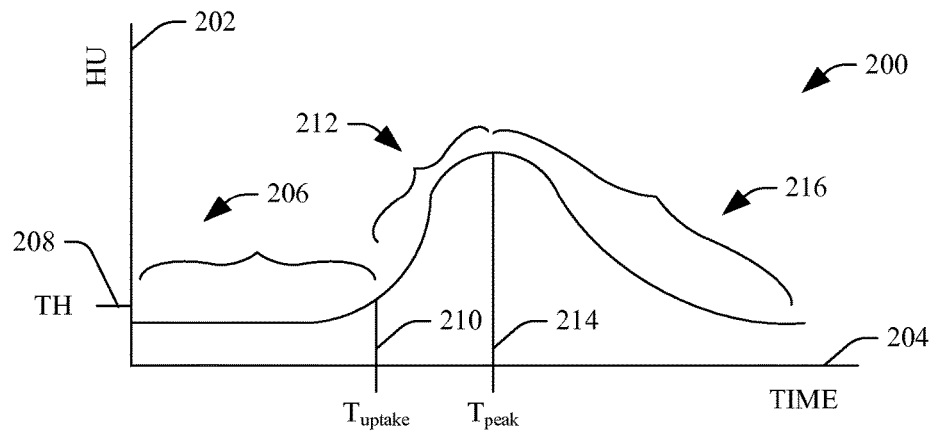
FIG. 2 shows an example graph of contrast uptake and wash out.

FIG. 2 illustrates an example curve 200 of contrast uptake and wash out. In FIG. 2, a y-axis 202 represents an amount of contrast at a given location of tissue of interest and an x-axis 204 represents time. In this example, the amount of contrast at the given location can be determined based on the Hounsfield Unit (HU) values of the voxels representing the given location in the image data corresponding to the given location of the tissue of interest.

In this example, during a region 206, after the contrast has been administered but before the contrast reaches the given location of the tissue of interest, the voxel value is below a predetermined threshold value (TH) 208 representing sufficient presence of contrast at the given location of the tissue of interest. The Hounsfield Unit (HU) values during this region represent baseline values. Although the portion of the curve 200 in the region 206 is shown as a straight line, the portion may fluctuate due to blood flow, movement, etc.

In this example, at time ($T_{uptake}$) 210, the voxel value satisfies the threshold 208, indicating sufficient presence of contrast at the given location of the tissue of interest. During a region 212, the voxel value continues to rise, indicating contrast uptake. At time ($T_{peak}$) 214, the voxel value reaches a peak HU value. During a region 216, the voxel value decreases, indicating contrast wash out.

It is to be appreciated that for a given sampling rate, the output of the radiation source can be selectively reduced or increased during the scan based on a user preference, a default setting, etc.

Figure 3:
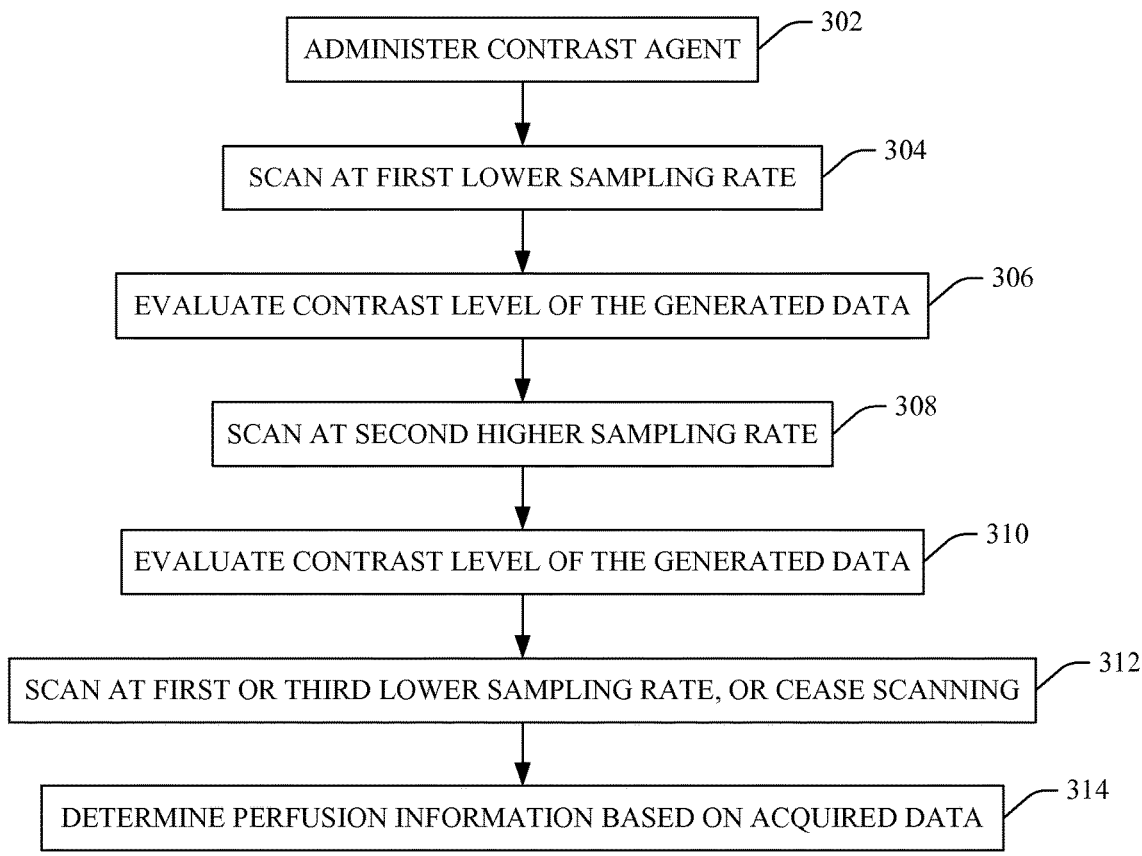
FIG. 3 illustrates a method.

FIG. 3 illustrates a method of dynamically adjusting a frequency of data acquisition sampling rate during a CTP scan in connection with the contrast uptake curve 200 of FIG. 2.

At 302, a contrast agent is administered to a subject.

At 304, the subject is scanned at a first data acquisition sampling rate. The first data acquisition sampling rate can be set based on a scan protocol (e.g., the dynamic perfusion scan protocol 124) or, manually, by an operator of the system. In one instance, the first data acquisition sampling rate is variable and increased over time or as it gets close to a predetermined typical uptake point, thereby facilitating identifying the uptake point. By way of example, the scan may begin with sampling at a first sampling rate for a first time duration, then at a higher sampling rate for a next time duration, and then at an even higher sampling rate until uptake is detected. Other sampling rate variation patterns are also contemplated herein.

At 306, the projection and/or image data is evaluated to determine whether a threshold level of contrast has reached a given location of tissue of interest. As discussed herein, this can be achieved by tracking the Hounsfield Unit value. The threshold level can be set based on the scan protocol or, manually, by an operator of the system.

At 308, in response to the level of contrast reaching the threshold level, the data acquisition sampling rate is increased to a second data acquisition sampling rate, which, in general, is higher than the first data acquisition sampling rate. The second data acquisition sampling rate can be set based on the scan protocol or, manually, by an operator of the system. The sampling duration can also be increased along with the increased sampling rate, which may facilitate maintaining or still reducing overall dose of the scan, but providing additional image data during the important period.

At 310, the projection and/or image data is evaluated to determine whether a peak level or wash out level of contrast has reached the given location of tissue of interest. Again, this can be achieved by tracking the Hounsfield Unit value. The wash out level can be set based on the scan protocol or, manually, by an operator of the system.

At 312, in response to the level of contrast reaching the peak level, the data acquisition sampling rate can be, at some predetermined time thereafter, maintained, decreased to the first data acquisition sampling rate, or decreased to a third data acquisition sampling rate, which is between the first and the second data acquisition sampling rates. The third data acquisition sampling rate can be set based on the scan protocol or, manually, by an operator of the system. In another instance, the scanning ceases in response to the level of contrast reaching the peak level or some predetermined time thereafter.

At 314, the acquired data is utilized to determine perfusion related information. Such information may include, but is not limited to, blood flow, blood volume, mean transit time and time to peak, perfusion maps, and/or summary maps graphically show the perfusion status.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer. The acts need not be performed concurrently with data acquisition.

In the above, the data acquisition sampling rates are functions of time and contrast uptake curve. On the other hand, the desired data acquisition phase is a function of the cardiac cycle and/or respiratory phase(s) thereof. By way of example, in connection with cardiac applications, scans are triggered by an ECG signal at the same physiological phase. In this instance, the system 100 further includes an ECG monitor or other device that can sense heart electrical activity. For abdomen and pulmonary applications, scans may be triggered based on a respiratory signal. In this instance, the system 100 further includes a respiratory bellow or the like.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
dynamically varying a data acquisition sample rate between at least two different data acquisition sample rates during a contrast enhanced perfusion scan of tissues of interest in a patient with a computed tomography (CT) scanner based on at least one predetermined level of a contrast in image data generated during the scan;
wherein the at least two different data acquisition sampling rates includes acquiring data at a first data acquisition sampling rate in an absence of a predetermined initial minimum level of contrast of the at least one predetermined level in the image data, and the first sampling rate is variable and increases over time; and wherein the at least two different data acquisition sampling rates includes acquiring data at a second predetermined data acquisition sampling rate during an uptake of the contrast and the first data acquisition sampling rate is less than the second predetermined data acquisition sampling rate, and the uptake starts with a concentration of the contrast exceeding the predetermined initial minimum level of the at least one predetermined level.

2. The method of claim 1, further comprising:
acquiring data at a third predetermined data acquisition sampling rate during a washout of the contrast and the third predetermined data acquisition sampling rate is less than the second predetermined data acquisition sampling rate, and the washout is determined by a decrease from a peak concentration of the contrast.

3. The method of claim 2, wherein, for a given sampling rate, selectively reducing or raising an x-ray source output during the scan based on a user preference.

4. The method of claim 1, further comprising:
comparing voxels values from the image data with a threshold value corresponding to the predetermined initial minimum level of the contrast; and
generating a signal indicative of the comparison.

5. The method of claim 4, further comprising:
determining the absence of the predetermined initial minimum level of contrast in response to the signal not satisfying the threshold value.

6. The method of claim 4, further comprising:
determining the uptake of the contrast in response to the signal satisfying the threshold value.

7. The method of claim 1, wherein at least one of the first or second data acquisition sampling rates is based on a scan protocol.

8. The method of claim 1, wherein at least one of the first or second data acquisition sampling rates is determined based on a signal indicative of a user input.

9. The method of claim 1, wherein a desired acquisition phase is a function of a cardiac phase of interest, and wherein acquiring data at the second predetermined data acquisition sampling rate is in response to detecting the cardiac phase of interest and during the uptake of the contrast.

10. The method of claim 1, wherein a desired acquisition phase is a function of a respiratory phase of interest, and wherein acquiring data at the second predetermined data acquisition sampling rate in response to detecting the respiratory phase of interest and during the uptake of the contrast.

11. A system, comprising:
a computed tomography (CT) scanner; and
a console including a computer configured to control the CT scanner based on a scan protocol, wherein the console dynamically varies a data acquisition sample rate of the CT scanner during a contrast enhanced perfusion scan based on at least one predetermined level of contrast in the image data generated during the scan, and the varied data acquisition sample rate includes a first data acquisition sampling rate in an absence of a predetermined initial minimum level of contrast in the image data, and the first sampling rate is variable and increases over time.

12. The system of claim 11, further comprising:
a data evaluator including a configured computer processor which determines levels of contrast in the image data indicated by at least one of substantially no contrast, an uptake of the contrast, or a wash-out of the contrast, and the uptake of the contrast is indicated by a concentration of the contrast exceeding a predetermined threshold level.

13. The system of claim 12, wherein the console controls the CT scanner to acquire data at a second data acquisition sampling rate in response to the data evaluator determining that the level of contrast in the image data indicates the uptake of the contrast, and the second data acquisition sampling rate is greater than the first data acquisition sampling rate.

14. The system of claim 13, wherein the console controls the CT scanner to acquire data at a third data acquisition sampling rate in response to the data evaluator determining that the level of contrast in the image data indicates the washout of the contrast, wherein third data acquisition sampling rate is one of equal to or less than the second data acquisition sampling rate, and the washout is determined by a decrease from a peak concentration of the contrast.

15. The system of claim 12, wherein an acquisition phase of the CT scanner corresponds to one of a cardiac phase of interest or a respiratory phase of interest.

16. A perfusion imaging method comprising:
acquiring data at a first sampling rate of tissues of interest in a patient with a computed tomography (CT) scanner until an uptake of a contrast has been determined, and the first sample rate is variable and increases over time; and
acquiring data at a second sampling rate of the tissues of interest in the patient with the computed tomography (CT) scanner, which is greater than the first sampling rate, during the uptake of the contrast, wherein the uptake begins with a concentration of the contrast exceeding a predetermined threshold level and the concentration of the contrast is increasing during the uptake.

17. The method of claim 16, further comprising:
acquiring data at a third sampling rate of the tissues of interest in the patient with the computed tomography (CT) scanner during a wash-out of the contrast, wherein the third sampling rate is less than the second sampling rate; and the wash-out is determined by a decrease from a peak concentration of the contrast.

18. The method of claim 16, further comprising:
varying scan dose in conjunction with at least one of the first and the second sampling rates.

19. The method of claim 16, further comprising:
increasing a sampling duration along with increasing at least one of the first and the second sampling rates.

* * * * *